United States Patent
Tsubouchi

(10) Patent No.: US 11,103,427 B2
(45) Date of Patent: Aug. 31, 2021

(54) AEROSOL COMPOSITION FOR HAIR AND AEROSOL PRODUCT FOR HAIR

(71) Applicant: TOYO AEROSOL INDUSTRY CO., LTD., Tokyo (JP)

(72) Inventor: Makoto Tsubouchi, Tokyo (JP)

(73) Assignee: TOYO AEROSOL INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 16/574,947

(22) Filed: Sep. 18, 2019

(65) Prior Publication Data

US 2020/0009026 A1  Jan. 9, 2020

Related U.S. Application Data

(63) Continuation of application No. PCT/JP2017/038139, filed on Oct. 23, 2017.

(30) Foreign Application Priority Data

May 23, 2017  (JP) .............. JP2017-101569

(51) Int. Cl.
- *A61K 8/04* (2006.01)
- *A61K 8/31* (2006.01)
- *A61K 8/34* (2006.01)
- *A61K 8/73* (2006.01)
- *A61Q 5/02* (2006.01)

(52) U.S. Cl.
CPC ............ *A61K 8/046* (2013.01); *A61K 8/31* (2013.01); *A61K 8/345* (2013.01); *A61K 8/732* (2013.01); *A61Q 5/02* (2013.01)

(58) Field of Classification Search
CPC .......... A61K 8/046; A61K 8/31; A61K 8/732; A61K 8/345; A61Q 5/02
See application file for complete search history.

(56) References Cited

U.S. PATENT DOCUMENTS

| | | |
|---|---|---|
| 2012/0282190 A1 | 11/2012 | Hammer |
| 2014/0000642 A1 | 1/2014 | Swaile et al. |
| 2014/0000643 A1 | 1/2014 | Swaile et al. |
| 2014/0283865 A1 | 9/2014 | Avery et al. |
| 2017/0000718 A1 | 1/2017 | Swaile et al. |
| 2017/0000719 A1 | 1/2017 | Swaile et al. |

FOREIGN PATENT DOCUMENTS

| | | |
|---|---|---|
| EP | 0370764 A2 | 5/1990 |
| EP | 0948960 A2 | 10/1999 |
| JP | H02-294382 A | 12/1990 |
| JP | H05-139932 A | 6/1993 |
| JP | H05-262616 A | 10/1993 |
| JP | 2000026242 A | 1/2000 |
| JP | 2001302445 A | 10/2001 |
| JP | 2002087943 A | 3/2002 |
| JP | 2002255756 A | 9/2002 |
| JP | 2007001991 A | 1/2007 |
| JP | 2007217314 A | 8/2007 |
| JP | 2011213619 A | 10/2011 |
| JP | 2013227249 A | 11/2013 |
| JP | 2014133717 A | 7/2014 |
| JP | 2014521732 A | 8/2014 |
| JP | 2015519407 A | 7/2015 |
| JP | 2015520246 A | 7/2015 |
| WO | 2011/056625 A1 | 5/2011 |
| WO | 2013026630 A2 | 2/2013 |

OTHER PUBLICATIONS

First Examination Report for the corresponding Indian patent Application No. 201937037903 dated Mar. 21, 2020 and English translation.
International Search Report dated Jan. 23, 2018 for PCT/JP2017/038139 and English translation.
Notice of Reasons for Refusal of corresponding Japanese application 2018-509625 dated Mar. 20, 2018 and its English translation.
EPO, Extended European Search Report for the corresponding European patent application No. 17911135.6, dated Dec. 17, 2019.

*Primary Examiner* — Zohreh A Fay

(74) *Attorney, Agent, or Firm* — Lucas & Mercanti, LLP

(57) ABSTRACT

The present invention has as its object the provision of an aerosol composition for hair which has excellent deodorization effect and silky feeling and in which a powder hardly floats at an applied area, and an aerosol product for hair. An aerosol composition for hair of the present invention is characterized by comprising: 2 to 7% by mass of an oil absorbing powder having an oil absorption of 0.45 to 0.75 ml/g; 0.1 to 0.6% by mass of a polyol; 3 to 33% by mass of a lower alcohol; and 65 to 94% by mass of a hydrocarbon having 3 to 5 carbon atoms which has a vapor pressure of 0.05 to 0.35 MPa at a temperature of 20° C.; and containing no surfactant. An aerosol product for hair of the present invention is characterized by comprising the aerosol composition for hair filled in an aerosol container which is a pressure-resistant container having an aerosol valve, and in that the discharge amount is 0.3 to 1.2 g/second.

4 Claims, No Drawings

AEROSOL COMPOSITION FOR HAIR AND AEROSOL PRODUCT FOR HAIR

CROSS REFERENCE TO RELATED APPLICATIONS

This Application is a continuation of PCT/JP2017/038139 filed on Oct. 23, 2017, which, in turn, claimed the priority of Japanese Patent Application No. 2017-101569 filed on May 23, 2017, both applications are incorporated herein by reference.

TECHNICAL FIELD

The present invention relates to an aerosol composition for hair and an aerosol product for hair.

BACKGROUND ART

Conventionally, an aerosol composition which contains a powder acting as an oil absorbent and a deodorant, such as a starch, and is used as a dry shampoo or the like has been known as a certain type of aerosol composition for hair (for example, see Patent Literatures 1 and 2).

Specifically, Patent Literature 1 discloses a kit for cleaning hair including an aerosol composition containing a powder and a non-woven fabric impregnated with a surfactant, wherein hair is cleaned by applying the aerosol composition to hair and wiping an area, in which the aerosol composition has been applied, with the non-woven fabric impregnated with the surfactant.

Patent Literature 2 discloses an aerosol composition which contains a tapioca starch and is used as a dry shampoo.

When the proportion of the powder is especially high in such an aerosol composition for hair containing a powder, the powder remains on hair to cause white residue (floating powder) as a problem. When a surfactant is applied, a sticky feeling caused by the surfactant is provided at an applied area. Therefore, there is a problem in which a silky feeling obtained by an effect of the powder is not sufficiently provided to give no comfort during use.

CITATION LIST

Patent Literature

Patent Literature 1: Japanese Translation of PCT Patent Application Publication No. 2014-521732
Patent Literature 1: Japanese Translation of PCT Patent Application Publication No. 2015-520246

SUMMARY OF INVENTION

Technical Problem

The present invention has been made in view of the foregoing circumstances and has as its object the provision of an aerosol composition for hair which has excellent deodorization effect and silky feeling and in which a powder hardly floats at an applied area, and an aerosol product for hair.

Solution to Problem

An aerosol composition for hair of the present invention includes 2 to 7% by mass of an oil absorbing powder having an oil absorption of 0.45 to 0.75 ml/g, 0.1 to 0.6% by mass of a polyol, 3 to 33% by mass of a lower alcohol, and 65 to 94% by mass of a hydrocarbon having 3 to 5 carbon atoms which has a vapor pressure of 0.05 to 0.35 MPa at a temperature of 20° C., and contains no surfactant.

In the aerosol composition for hair of the present invention, it is preferable that the proportion of the oil absorbing powder is 3 to 5% by mass, the proportion of the polyol is 0.1 to 0.3% by mass, the proportion of the lower alcohol is 12 to 33% by mass, and the proportion of the hydrocarbon is 65 to 83% by mass.

In the aerosol composition for hair of the present invention, it is preferable that the oil absorbing powder is one or two or more types selected from the group consisting of a corn starch, a rice starch, a tapioca starch, a potato starch, a wheat starch, a siliconate-modified starch, aluminum starch octenylsuccinate, cellulose and silica.

The aerosol product for hair of the present invention is an aerosol product for hair in which the aerosol composition for hair is filled in an aerosol container which is a pressure-resistant container having an aerosol valve. In the aerosol product, the discharge amount is 0.3 to 1.2 g/second.

Advantageous Effects of Invention

The aerosol composition for hair of the present invention contains, in addition to an oil absorbing powder, a lower alcohol, a polyol, and a specific hydrocarbon at respective specific proportions. Therefore, a good dispersion state of the oil absorbing powder in the composition can be achieved without using a surfactant. Further, good discharge characteristics can be obtained, and a discharged substance may have good attachment to an applied area. As the oil absorbing powder, an oil absorbing powder having a specific oil absorption is used, and so the proportion of the oil absorbing powder can be relatively reduced. Therefore, while occurrence of so-called white residue (floating powder) at the applied area is suppressed, excellent deodorization effect can be achieved, and a silky feeling can be provided to scalp and hair.

According to the aerosol composition for hair of the present invention, excellent deodorization effect and silky feeling are obtained due to the oil absorbing powder without generating a sticky feeling due to the presence of surfactant, and occurrence of floating powder at the applied area is suppressed.

According to the aerosol product for hair of the present invention, the aerosol composition for hair of the present invention is filled in an aerosol container, and the discharge amount is set to fall within a specific range. Therefore, excellent deodorization effect and silky feeling are obtained, and occurrence of floating powder at the applied area is suppressed.

DESCRIPTION OF EMBODIMENTS

An aerosol composition for hair of the present invention contains a specific oil absorbing powder, a polyol, a lower alcohol, and a specific hydrocarbon as essential components at respective specific proportions, and does not contain a surfactant.

In the aerosol composition for hair of the present invention, the polyol, the lower alcohol, the specific oil absorbing powder and an optional component to be contained as necessary constitute a liquid concentrate, and the specific hydrocarbon constitutes a propellant. The liquid concentrate is provided in a state where the oil absorbing powder is dispersed in a dispersion medium containing the polyol and the lower alcohol.

Hereinafter, components constituting the aerosol composition for hair of the present invention will be described.

Oil Absorbing Powder:

The oil absorbing powder which is an essential component mainly acts as an oil absorbent and a deodorant, and expresses a silky feeling at an applied area.

The oil absorbing powder is a powder having an oil absorption of 0.45 to 0.75 ml/g.

In the invention of the present application, "oil absorption" means the amount of oil capable of being carried on an oil absorbing powder, and specifically shows a value specified by the amount of squalane absorbed into the oil absorbing powder. The value is calculated by the following expression (1). In the expression (1), O [ml/g] is an "oil absorption," V [ml] is the "amount (ml) of squalane used until a softening phenomenon occurs," and P [g] is the "amount of oil absorbing powder." The "amount of squalane used until a softening phenomenon occurs" is the amount of squalane required until an aggregate (lump) in which the oil absorbing powder is aggregated causes a softening phenomenon. Specifically, a kneading operation in which squalane is added dropwise to P g of an oil absorbing powder on a glass plate from a burette and the whole oil absorbing powder is kneaded by an iron spatula after each addition is repeated. Through such a process, the oil absorbing powder is aggregated and solidified, and a softening phenomenon where the aggregate is abruptly softened by dropwise addition of squalane occurs. The amount of squalane used until a softening phenomenon occurs is the total amount of squalane added dropwise to the oil absorbing powder until such a softening phenomenon occurs.

$$O[ml/g] = V[ml]/P[g] \quad \text{Expression (1)}$$

When the oil absorption in the oil absorbing powder is too large, hair may be creaked at the applied area due to excessive removal of sebum.

In contrast, when the oil absorption is too small, sufficient deodorization effect and silky feeling may not be obtained.

In the aerosol composition for hair of the present invention, it is preferable to use one or two or more types of powders selected from the group consisting of a corn starch, a rice starch, a tapioca starch, a potato starch, a wheat starch, a siliconate-modified starch, aluminum starch octenylsuccinate, cellulose and silica as the oil absorbing powder.

As the oil absorbing powder in the aerosol composition for hair of the present invention, a rice starch, aluminum starch octenylsuccinate and a mixture (mixed powder) of aluminum starch octenylsuccinate and silica are preferable.

In the aerosol composition for hair of the present invention, when the oil absorbing powder is a mixture, that is, a mixture containing two or more types of powders, the oil absorption of the mixture may be 0.45 to 0.75 ml/g. In each of the powders constituting the mixture, the oil absorption may or may not fall within a range of 0.45 to 0.75 ml/g.

It is preferable that the average particle size of the oil absorbing powder is 1 to 30 μm.

If the average particle size of the oil absorbing powder is too large, a feeling of roughness may be provided at the applied area. In the aerosol product, the aerosol valve may be easily clogged.

In contrast, if the average particle size of the oil absorbing powder is too small, the human body may be adversely affected.

The proportion of the oil absorbing powder in the entire aerosol composition for hair is 2 to 7% by mass, preferably 3 to 5% by mass.

If the proportion of the oil absorbing powder is too high, so-called white residue may occur (the powder may float) at the applied area. In the composition, the dispersion state of the oil absorbing powder may become unstable. Therefore, a sufficient dispersion state may not be achieved during use. Further, a discharged substance may not have sufficient attachment to the applied area. In the aerosol product, the aerosol valve may be easily clogged.

In contrast, if the proportion of the oil absorbing powder is too low, sufficient deodorization effect and silky feeling may not be obtained.

Polyol:

The polyol which is an essential component mainly acts as a spreading agent and expresses a moisturizing effect at the applied area.

As examples of the polyol, may be mentioned propylene glycol, dipropylene glycol, 1,3-butylene glycol, 1,3-propanediol, hexanediol, octanediol, glycerin and ethylhexylglycerin. These polyols may be used either singly or in any combination of two or more types.

As the polyol in the aerosol composition for hair of the present invention, propylene glycol and 1,3-butylene glycol are preferable.

The proportion of the polyol is 0.1 to 0.6% by mass, preferably 0.1 to 0.3% by mass, in the entire aerosol composition for hair.

If the proportion of the polyol is too high, a silky feeling may not be obtained.

In contrast, if the proportion of the polyol is too low, the discharged substance may not have sufficient attachment to the applied area.

Lower Alcohol:

The lower alcohol which is an essential component mainly acts as a dispersion medium of the oil absorbing powder, and expresses a refreshing effect and a quick-drying action at the applied area.

As examples of the low alcohol, may be mentioned alcohols having 2 to 3 carbon atoms such as ethanol and isopropanol. The lower alcohols may be used either singly or in any combination thereof.

From the viewpoint of dispersibility of the oil absorbing powder and miscibility with the polyol, the lower alcohol in the aerosol composition for hair of the present invention is preferably ethanol. When ethanol is used as the lower alcohol, comfort during use is obtained from the viewpoint of refreshing properties and quick-drying properties.

The proportion of the lower alcohol is 3 to 33% by mass, preferably 12 to 33% by mass, in the entire aerosol composition for hair.

When the proportion of the lower alcohol falls within the aforementioned range, a good dispersion state of the oil absorbing powder in the composition can be obtained, and sufficient refreshing properties and quick-drying properties can be achieved.

In contrast, if the proportion of the lower alcohol is too low, the discharged substance may not have sufficient attachment at the applied area.

Hydrocarbon:

The hydrocarbon which is an essential component is a hydrocarbon having 3 to 5 carbon atoms, which constitutes a propellant and has a vapor pressure of 0.05 to 0.35 MPa at a temperature of 20° C.

As specific examples of the hydrocarbon in the aerosol composition for hair of the present invention, may be mentioned propane, n-butane, iso-butane, n-pentane, iso-pentane and mixtures thereof.

If the vapor pressure of the hydrocarbon at a temperature of 20° C. is too high, the power of discharge is too high, and sufficient attachment is not achieved. Therefore, a silky feeling may not be obtained. Due to excessively high internal pressure of the product, sufficient safety may not be obtained.

In contrast, if the vapor pressure of the hydrocarbon at a temperature of 20° C. is too low, good discharge characteristics may not be obtained.

The proportion of the hydrocarbon is 65 to 94% by mass, preferably 65 to 83% by mass, in the entire aerosol composition for hair.

If the proportion of the hydrocarbon is too high, the discharged substance may not have sufficient attachment to the applied area. This is because the polyol and the lower alcohol cannot be blended at a sufficient proportion. Further, frostbite or the like may occur at the applied area.

In contrast, if the proportion of the hydrocarbon is too low, quick-drying properties may not be obtained. Further, good discharge characteristics are not obtained. In the aerosol product, the whole amount of the liquid concentrate filled in the aerosol container cannot be discharged. That is, the whole amount of the composition filled in the aerosol container may not be used. In the aerosol product, the aerosol valve may be easily clogged.

Optional Components:

The aerosol composition for hair of the present invention may contain optional components as necessary in addition to the essential components (oil-absorbing powder, polyol, lower alcohol and hydrocarbon).

As specific examples of the optional components, may be mentioned a cooling agent, a bactericide, a disinfectant, a plant extract, an anti-inflammatory agent, an antioxidant, an ultraviolet light absorber, a chelating agent, a preservative, a moisturizer, oils and fats, silicones and perfume.

The proportion of the optional component is appropriately determined on the basis of the use application of the composition and the like.

The aerosol composition for hair of the present invention is filled in the aerosol container which is a pressure-resistant container having an aerosol valve to obtain an aerosol product.

The aerosol product for hair of the present invention is characterized in that the aerosol composition for hair of the present invention is filled in the aerosol container, and the discharge amount is 0.3 to 1.2 g/second.

In the aerosol product for hair of the present invention, the discharge amount is 0.3 to 1.2 g/second. Therefore, the discharged substance does not excessively scatter during application and sufficient silky feeling and deodorization effect are obtained.

If the discharge amount is too large, the discharged substance may be inhaled due to excessive scattering, and the powder may float at the applied area.

In contrast, if the discharge amount is too small, sufficient silky feeling and deodorization effect may not be obtained.

In the aerosol composition for hair of the present invention as described above, an oil absorbing powder having a specific oil absorption is used as the oil absorbing powder, and so the proportion of the oil absorbing powder can be relatively reduced. Therefore, while occurrence of so-called white residue (floating powder) at the applied area is suppressed, excellent deodorization effect can be achieved, and a silky feeling can be provided to scalp and hair. In addition to the oil absorbing powder, the aerosol composition for hair of the present invention contains the lower alcohol, the polyol and the specific hydrocarbon at the respective specific proportions. Therefore, a good dispersion state of the oil absorbing powder in the composition can be achieved without using a surfactant. Further, good discharge characteristics can be obtained, and the discharged substance can have good attachment to the applied area.

According to the aerosol composition for hair of the present invention, excellent deodorization effect and silky feeling are obtained due to the oil absorbing powder without causing a sticky feeling due to the presence of surfactant, and occurrence of floating powder at the applied area is suppressed.

According to the aerosol product for hair of the present invention, the aerosol composition for hair of the present invention is filled in the aerosol container, and the discharge amount is set to fall within the specific range. Therefore, excellent deodorization effect and silky feeling are obtained, and occurrence of floating powder at the applied area is suppressed.

The aerosol composition for hair of the present invention and the aerosol product for hair of the present invention can be suitably used as a dry shampoo and a dry shampoo spray.

EXAMPLES

Hereinafter, Examples of the present invention will be described, but the present invention is not limited thereto.

Examples 1 to 4 and Comparative Examples 1 to 6

First, composition materials shown in Table 1 below were prepared. In the prepared composition materials, the oil absorption of oil absorbing powder was measured by the following procedure. The results are shown in Table 1.

Subsequently, the composition materials were filled in an aerosol container which was a pressure-resistant container having an aerosol valve at respective proportions shown in Table 1, to produce an aerosol product for evaluation.

Example 3 was an example of a case where as an oil absorbing powder, a mixture (mixed powders) having an oil absorption of 0.60 ml/g obtained by mixing aluminum starch octenylsuccinate (oil absorption: 0.51 ml/g) and silica (oil absorption: 1.1 ml/g) was used. Comparative Example 1 was an example of a case where the oil absorption of oil absorbing powder was too large. Comparative Example 2 was an example of a case where the vapor pressure of hydrocarbon was too high. Comparative Example 3 was an example of a case where the proportion of polyol was too high. Comparative Example 4 was an example of a case where the proportion of oil absorbing powder was too high. Comparative Example 5 was an example of a case where the proportion of oil absorbing powder was too low. Comparative Example 6 was an example of a case where the proportion of lower alcohol was too high and the proportion of hydrocarbon is too low.

The aerosol products for evaluation were each discharged to hair of each of ten subjects for about five seconds, and the hair was combed five times at an applied area. After that, sensory tests were performed. In the sensory tests, whether a silky feeling of scalp was satisfied, whether the hair was creaked, whether white residue was seen, and whether odor of sebum was removed were confirmed. In accordance with the following evaluation criteria, the silky feeling of scalp, creaking of hair, white residue and deodorization effect (against the odor of sebum) were evaluated. The results are shown in Table 1.

For the content of each of the obtained aerosol products for evaluation, that was, the aerosol composition, the dispersibility was confirmed and evaluated according to the following procedure. The results are shown in Table 1.

Measurement of Oil Absorption of Oil Absorbing Powder:

On a glass plate, 1 g of oil absorbing powder was placed, squalane was added dropwise to the oil absorbing powder from a burette, and a kneading operation of kneading the whole oil absorbing powder by an iron spatula after each addition was repeated. In the repeated operation, the oil absorbing powder on the glass plate was aggregated and solidified. After that, when a softening phenomenon where the aggregate was abruptly softened by dropwise addition of squalane occurred, the dropwise addition of squalane was terminated. On the basis of the amount of squalane used until the softening phenomenon occurred (the amount of squalane used until the occurrence of softening phenomenon), the oil absorption of the oil absorbing powder was calculated by the expression (1) above.

Silky Feeling of Scalp:

A: A case where not less than eight subjects satisfied a silky feeling of scalp

B: A case where five to seven subjects satisfied a silky feeling of scalp

C: A case where three or four subjects satisfied a silky feeling of scalp

D: A case where not more than two subjects satisfied a silky feeling of scalp

Creaking of Hair:

A: A case where not more than two subjects satisfied a creaking feeling of hair

B: A case where three or four subjects satisfied a creaking feeling of hair

C: A case where five to seven subjects satisfied a creaking feeling of hair

D: A case where not less than eight subjects satisfied a creaking feeling of hair White Residue:

A: A case where not more than two subjects was concerned about white residue

B: A case where three or four subjects was concerned about white residue

C: A case where five to seven subjects was concerned about white residue

D: A case where not less than eight subjects was concerned about white residue

Deodorization Effect (Odor of Sebum):

A: A case where not less than eight subjects felt that the odor of sebum was removed B: A case where five to seven subjects felt that the odor of sebum was removed C: A case where three or four subjects felt that the odor of sebum was removed D: A case where not more than two subjects felt that the odor of sebum was removed Dispersibility of Aerosol Composition:

The aerosol composition according to the aerosol product for evaluation was placed in a glass bottle for aerosol, and was allowed to stand for 3 days under a condition of a temperature of 45° C. After that, the glass bottle for aerosol was shaken vertically, and the dispersion state of the oil absorbing powder was visually confirmed. The dispersibility was evaluated in accordance with the following evaluation criteria.

Evaluation Criteria of Dispersibility:

A: A case where the oil absorbing powder was completely dispersed by one to three shakings B: A case where the oil absorbing powder was completely dispersed by four to six shakings C: A case where the oil absorbing powder was completely dispersed by seven to nine shakings D: A case where not less than ten shakings are required for complete dispersion of the oil absorbing powder

TABLE 1

| | | | Example | | | | Comparative Example | | | | | |
|---|---|---|---|---|---|---|---|---|---|---|---|---|
| | | | 1 | 2 | 3 | 4 | 1 | 2 | 3 | 4 | 5 | 6 |
| Composition (% by mass) | Lower alcohol | Ethanol | 16.85 | 12.85 | 14.85 | 14.50 | 14.85 | 15.85 | 14.00 | 9.85 | 18.85 | 45.85 |
| | polyol | Propylene glycol | 0.15 | 0.15 | 0.15 | — | 0.15 | 0.15 | 2.00 | 0.15 | 0.15 | 0.15 |
| | | 1,3-Butylene glycol | — | — | — | 0.50 | — | — | — | — | — | — |
| | Oil absorbing powder | Aluminum starch octenylsuccinate | — | 7.00 | 4.85 | 5.00 | — | 4.00 | 4.00 | 10.00 | 1.00 | 4.00 |
| | | Rice starch | 3.00 | — | — | — | — | — | — | — | — | — |
| | | Silica | — | — | 0.15 | — | 5.00 | — | — | — | — | — |
| | | Total of oil absorbing powder | 3.00 | 7.00 | 5.00 | 5.00 | 5.00 | 4.00 | 4.00 | 10.00 | 1.00 | 4.00 |
| | Hydrocarbon | LPG0.25 MPa (at 20° C.) | 80.00 | 80.00 | 80.00 | 80.00 | 80.00 | — | 80.00 | 80.00 | 80.00 | 50.00 |
| | | LPG0.44 MPa (at 20° C.) | — | — | — | — | — | 80.00 | — | — | — | — |
| | | Total | 100.00 | 100.00 | 100.00 | 100.00 | 100.00 | 100.00 | 100.00 | 100.00 | 100.00 | 100.00 |
| Oil absorption of oil absorbing powder (ml/g) | | | 0.49 | 0.51 | 0.60 | 0.51 | 1.1 | 0.51 | 0.51 | 0.51 | 0.51 | 0.51 |
| Discharge amount (g/second) | | | 0.78 | 0.67 | 0.84 | 0.75 | 0.72 | 1.34 | 0.85 | 0.78 | 0.63 | 1.1 |
| Evaluation | Dispersibility of oil absorbing powder | | B | B | A | B | B | B | B | C | A | C |
| | Silky feeling of scalp | | B | A | A | A | A | C | D | A | D | C |
| | Creaking of hair | | A | A | B | A | D | A | A | A | A | B |
| | White residue | | B | B | A | B | D | A | B | D | A | A |
| | Deodorization effect (odor of sebum) | | B | B | B | B | B | B | B | B | C | B |

In Table 1, "aluminum starch octenylsuccinate" shows "OCTIE" manufactured by Nippon Starch Chemical Co., Ltd., "rice starch" shows "Rice starch" manufactured by JAPAN CORN STARCH CO., Ltd., "silica" shows "cosmetic silica QC4" manufactured by FUJI SILYSIA CHEMICAL LTD., and "tapioca starch" shows "Naviance Tapioca PLM" manufactured by Akzo Nobel N.V.

From these results, it is confirmed that in the aerosol products of the present invention according to Examples 1 to 4, excellent deodorization effect and silky feeling are obtained and floating powder is hardly generated at an applied area.

It is confirmed that in the aerosol compositions according to Examples 1 to 4 of the present invention, a good dispersion state of the oil absorbing powder is achieved without blending a surfactant.

The invention claimed is:

1. An aerosol composition for hair, comprising: 3 to 5% by mass of an oil absorbing powder having an oil absorption of 0.45 to 0.75 ml/g; 0.1 to 0.6% by mass of a polyol; 3 to 17% by mass of a lower alcohol; and 65 to 94% by mass of a hydrocarbon having 3 to 5 carbon atoms which has a vapor pressure of 0.05 to 0.35 MPa at a temperature of 20° C.; and containing no surfactant.

2. The aerosol composition for hair according to claim 1, wherein a proportion of the polyol is 0.1 to 0.3% by mass, a proportion of the lower alcohol is 12 to 17% by mass, and a proportion of the hydrocarbon is 65 to 83% by mass.

3. The aerosol composition for hair according to claim 1, wherein the oil absorbing powder is one or two or more types selected from the group consisting of a corn starch, a rice starch, a tapioca starch, a potato starch, a wheat starch, a siliconate-modified starch, aluminum starch octenylsuccinate, cellulose and silica.

4. An aerosol product for hair, comprising the aerosol composition for hair according to claim 1 filled in an aerosol container which is a pressure-resistant container having an aerosol valve, wherein a discharge amount is 0.3 to 1.2 g/second.

* * * * *